United States Patent
Sparg

(10) Patent No.: US 9,832,997 B2
(45) Date of Patent: Dec. 5, 2017

(54) METHODS OF AND APPARATUS FOR EXTRACTING 3-METHYL-2H-FURO[2,3-C]PYRAN-2-ONE

(76) Inventor: Shane Gordon Sparg, Centurion (ZA)

(*) Notice: Subject to any disclaimer, the term of this patent is extended or adjusted under 35 U.S.C. 154(b) by 268 days.

(21) Appl. No.: 13/261,779

(22) PCT Filed: May 16, 2012

(86) PCT No.: PCT/ZA2012/000031
§ 371 (c)(1),
(2), (4) Date: Nov. 15, 2013

(87) PCT Pub. No.: WO2012/159129
PCT Pub. Date: Nov. 22, 2012

(65) Prior Publication Data
US 2014/0243204 A1 Aug. 28, 2014

(30) Foreign Application Priority Data

May 16, 2011 (ZA) ................................. 2011/03553

(51) Int. Cl.
*A01N 43/90* (2006.01)
*A01N 25/18* (2006.01)

(52) U.S. Cl.
CPC ............. *A01N 43/90* (2013.01); *A01N 25/18* (2013.01)

(58) Field of Classification Search
CPC ...................................................... A01N 43/90
See application file for complete search history.

(56) References Cited

U.S. PATENT DOCUMENTS

| | | | |
|---|---|---|---|
| 3,106,473 A | 10/1963 | Hollenbeck | |
| 7,758,818 B2 * | 7/2010 | Lee et al. | ....................... 422/168 |
| 2007/0053803 A1 | 3/2007 | Lee et al. | |

FOREIGN PATENT DOCUMENTS

| | | |
|---|---|---|
| DE | 102006027882 A1 | 3/2007 |
| JP | 2004141839 A | 5/2004 |
| WO | WO 2005061515 A1 * | 7/2005 |
| WO | WO 2005061515 A1 | 7/2005 |

OTHER PUBLICATIONS

Chiwocha S D S et al, "Karrikins: A new family of plant growth regulators in smoke", Plant Science vol. 177 No. 4, XP026391147, ISSN10-21-2009, p. 252-256.

Marnie E. Light et al, "Butenolides from Plant-Derived Smoke: Natural Plant-Growth Regulators with Antagonistic Actions on Seed Germination".

Journal of Natural Products vol. 73 No. 2, Feb. 26, 2010 pp. 267-269 XP055158504, ISSN: 0163-3864, DOI: 10.1021/np900630w, abstract, p. 267, left-hand column to line 12 right hand column; compounds 1,2; p. 268 right-hand column, lines 24-37.

* cited by examiner

*Primary Examiner* — Noble Jarrell
*Assistant Examiner* — John S Kenyon

(57) ABSTRACT

A method for extracting the compound 3-methyl-2H-furo[2,3-c]pyran-2-one from smoke, the method comprising pyrolysis of cellulose or any biomass within a combustion chamber, directing the smoke into a scrubbing apparatus incorporating a spiral condenser tube extending along the chamber and having a number of mist spray units spaced along the entire spiral condenser tube, collecting smoke water thus formed and passing it to a cooling chamber and then to preparation for storage or despatch.

5 Claims, 2 Drawing Sheets

METHODS OF AND APPARATUS FOR EXTRACTING 3-METHYL-2H-FURO[2,3-C]PYRAN-2-ONE

Figure 1:
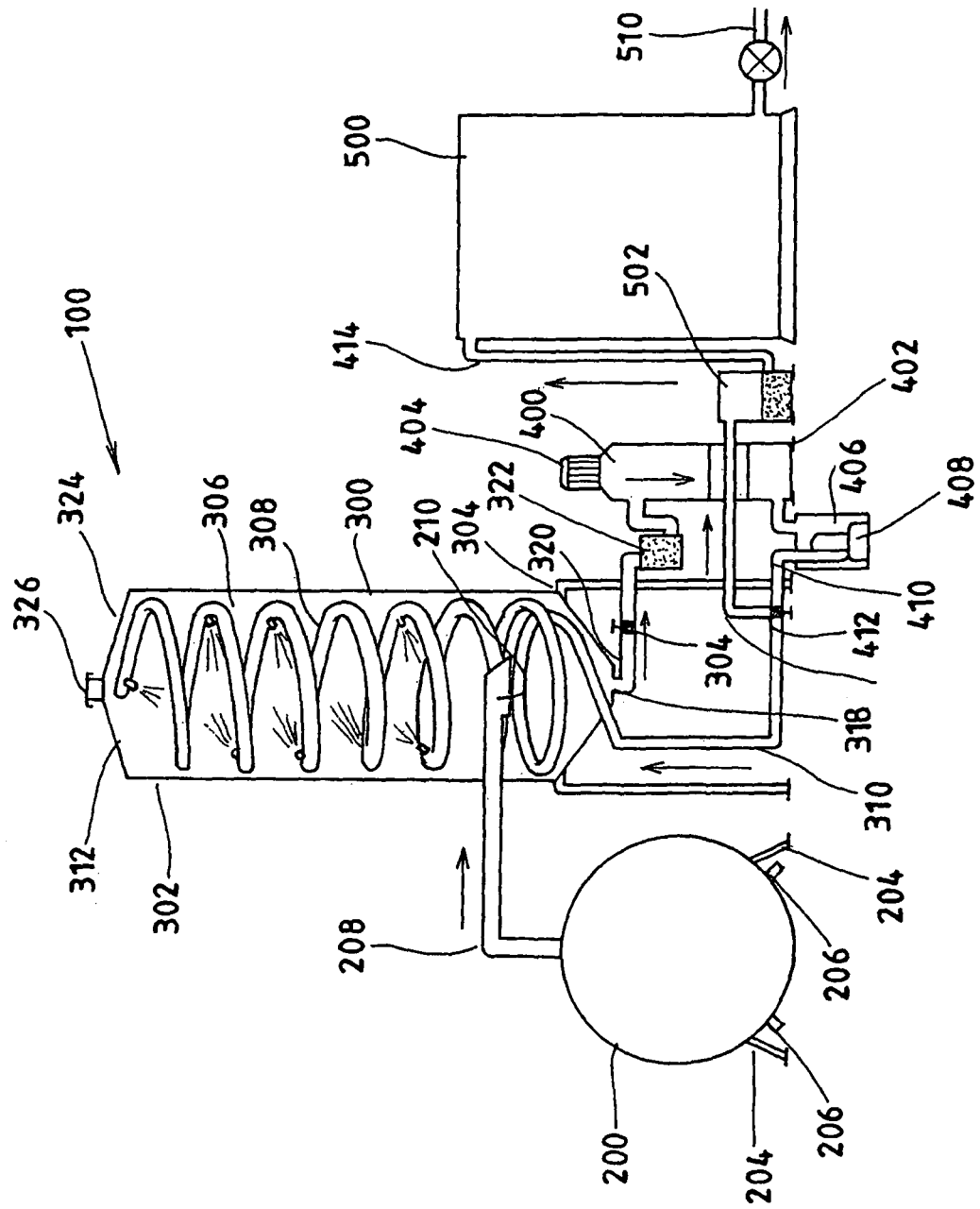

This is a U.S. National Phase Entry of PCT Application No. PCT/ZA2012/000031 filed May 16, 2012 with a priority date of May 16, 2011 based upon Application No ZA 2011/03553 filed in South Africa.

This invention relates to methods of and apparatus for extracting 3-methyl-2H-furo[2,3-c]pyran-2-one.

A method of extracting 3-methyl-2H-furo[2,3-c]pyran-2-one and the methods of and advantages of using 3-methyl-2H-furo[2,3-c]pyran-2-one are described in WO 2005/061515 (Botanical Gardens and Parks Authority) and in South African patent specification No 2006/06816 (Sparg and others). As described in the foregoing documents, a solution of 3-methyl-2H-furo[2,3-c]pyran-2-one in water (hereinafter called "smoke water") is formed as follows: plant material is burned and the smoke is forced by means of air pumps into a volume of water for a set period of time. The resultant crude solution has been applied to a number of plant seed and seedlings and found to promote germination and vigour. Unfortunately the process has been found to be messy and not commercially viable.

It is an object of the invention to provide a method of producing smoke water which can be commercially viable.

According to one aspect of the invention there is provided a method of producing smoke water comprising
pyrolysis of cellulose or biomass in the presence of oxygen, preferably at a temperature of between about 160° C. and 200° C. and more preferably at about 280° C.;
extracting the smoke;
exposing the hot smoke to a cooling aqueous mist within a scrubbing chamber; and
then passing the smoke water that is discharged from the scrubbing chamber into a cooling chamber from which it passes to preparation for storage or despatch.

The cellulose or biomass is preferably of a size that will permit adequate burning. The pyrolysis preferably is completed within one hour.

Preferably the smoke and smoke water are cooled by a condenser in the scrubbing chamber. This condenser serves to spray mist into the scrubbing chamber.

According to another aspect of the invention there is provided apparatus for making smoke water containing 3-methyl-2H-furo[2,3-c]pyran-2-one comprising:
a combustion chamber having an outlet conduit through which smoke is discharged;
a scrubber having a chamber with an inlet to which the conduit is connected and an outlet for the condensed smoke solution;
a cooler connected to the said outlet, conveniently through filtering apparatus, and being connected to a discharge unit, preferably containing a filter device for removing impurities and solids, and thence to a maturation device for storage and or despatch of the smoke water.

The scrubber preferably comprises an internal condenser, preferably a spiral condenser, having mist spray nozzles for spraying mist into the scrubber chamber to cool the smoke entering the scrubber chamber and to form therewith smoke water. The cooler is preferably connected to the condenser to supply cooled aqueous smoke to the condenser to be discharged thereby through the spray nozzles. Near the upper end of the scrubber chamber, the condenser has a spray head through which remaining aqueous smoke can be discharged from the condenser into the chamber. The spray nozzles preferably are arranged to spray liquid droplets of sizes 500 μm to 5500 μm and in suitable patterns which may be air atomising fine spray cone or fan patterns or combinations thereof.

A pump means is preferably provided to pump smoke from the cooler to condenser and preferably also to the upper mist spray nozzles.

According to another aspect of the invention there is provided smoke water when produced by the method described above or in the apparatus described above.

An embodiment of the invention will now be described by way of example with reference to the accompanying drawings.

In the drawings:—

Figure 2:
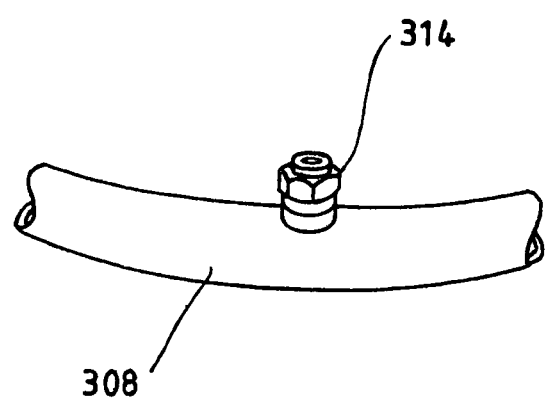

FIG. 1 is a schematic longitudinal section view of the apparatus of the invention for making smoke water; and FIG. 2 is a detail of a nozzle used for producing a mist spray.

Referring now to the drawing, there is shown apparatus 100 for producing smoke water containing 3-methyl-2H-furo[2,3-c]pyran-2-one in accordance with the invention. The apparatus 100 comprises a combustion chamber 200, a wet scrubber 300, a cooling tank 400 and a number of maturation tanks 500 (only one of which is shown) each having an outlet 510 leading to a bottling plant (not shown). Filtration devices to be described below are also provided.

The combustion chamber 200 is in the form of a horizontal cylindrical member 202 mounted on a suitable stand 204. The combustion chamber 200 is suitable for operating on a batch system. The capacity of the chamber 200 is one cubic meter so that it can contain approximately forty kilograms of cellulose normally in the form of dry grass. A suitable burner (not shown) or a pilot light is provided to ignite the cellulose. The combustion chamber 200 has a set of air inlet ports 206 whereby it is suitably vented to ambient air to enable oxygen to be drawn into the chamber to maintain pyrolysis. The ports 206 may be adjustable so that it is possible to maintain the temperature of burning cellulose at about 160° C. and 200° C. An outlet pipe 208 leads from the upper end of the chamber 200 to within the scrubber 300 where it, the outlet pipe 208, terminates in a downwardly directed inlet head 210 with appropriate discharge apertures (not shown).

The scrubber 300 comprises a vertical cylindrical housing 302 mounted on a stand 304 and defining an inner chamber 306. The capacity of the chamber 306 is the same as or greater than the capacity of the combustion chamber 200. Within the chamber 306 is a spiral condenser 308. The condenser 308 is fed at its lower end from a vertical tube 310 entering the chamber 306 at the lower end of the chamber. The condenser terminates near the upper end of the chamber 306 in a spray head 312.

From above a short distance from its lower end (about one third of its height) the spiral condenser 308 has a number of mist spray nozzles 314 (best shown in FIG. 2). The size of the mist spray nozzles 314 is such that the liquid discharged therefrom may be in the form of droplets of sizes of the order of 500 μm to 5500 μm preferably the smaller. The preferred diameter of the droplets that are actually provided is 1000 μm (i.e. one millimeter). The nozzles 314 are screwed into threaded nipples screwed into the wall of the condenser 308. The nozzles 314 are arranged to spray mist inwardly of the spiral, spraying liquid droplets in suitable patterns which may be air atomising fine spray cone or fan patterns or combinations thereof so as to ensure best mixing between the liquid sprayed from the nozzles and the smoke as will be described.

The outlet pipe 208 enters the chamber 306 a little below the height of the first spray nozzles 314 i.e. just below a third of the height of the chamber 306.

At the lower end of the chamber 306 is an outlet aperture 318 for the scrubbing filtrate water containing the compound 3-methyl-2H-furo[2,3-c]pyran-2-one (i.e. the smoke water). The outlet aperture 318 leads through a connector pipe 320 to the upper portion of the cooling tank 400. The smoke water can drain from the aperture 318 to the cooling tank 400. A filter 322 is provided in the connector pipe 320 to filter solids and impurities from the smoke water. An on off valve 304 is provided in the connector pipe 320 upstream of the filter 322.

At its upper end the chamber 302 has an upper conical part 324 having a suitably closed apex aperture 326 for maintenance of the chamber.

The cooling tank 400 is mounted on a stand 402. The tank 400 has a cooling fan 404 at its upper end and is refrigerated to cool aqueous solutions entering it. These solutions may be at a substantial temperature. Once cooled, the tank 400 must maintain a temperature of its contents of about 10° C. The tank 400 drains into a sump 406 which contains a circulating pump 408. The pump outlet pipe 410 is connected via a three way valve 412 to the vertical tube 310 and thence to the spiral condenser 308. In the reset position, the valve 412 is connected to a line 414 leading to the upper end of the maturation tank 500. An aggregate filter 502° C. is provided in the line 414 at a low level whereafter the line 414 extends upwardly to discharge into the upper end of the maturation tank 500. The tank 500 has an outlet pipe 510 at its lower end which leads to a bottling apparatus where the smoke water will be bottled preferably into twenty five liter bottles.

In use, the combustion chamber 200 is charged with cellulose in the form of grass that is preferably ground to a size that can maintain combustion. The pilot light is actuated to commence pyrolysis at about 160° C. to 200° C. The cooling tank 400 is charged with water which is cooled to 10° C. The valve 410 is adjusted to connect the pump outlet pipe 410 to the line 310 and thence the condenser 308. Once pyrolysis is underway and smoke is being discharged into the scrubber 300 via the line 208 and head 210, the pump 408 pumps the cold water into the spiral condenser or reticulation tube 308. The water is now sprayed in a fine mist by the nozzles 314. The smoke, which contains 3-methyl-2H-furo[2,3-c]pyran-2-one, is driven into intimate contact with the droplets being emitted by the nozzles so that the 3-methyl-2H-furo[2,3-c]pyran-2-one binds very effectively with the water. The smoke water thus formed now falls to the lower end of the chamber 306 and then through the connector pipe 320, through the filter 322 into the cooling tank 400 where it is cooled and from where it is recycled as described above.

After the charge in the combustion chamber 200 has been burned, the first valve 304 is closed and the second valve 412 is connected to the line 414. The smoke water is now delivered from the cooler tank 400 and sump 406 to the discharge pipe 414 (which now forms a discharge unit). It is now filtered in the filter mechanism 502 and then rests in the maturation tank 500 for a period of one week. Thereafter it is passed from the maturation tank 500 to the bottling plant. The solids in the bottled product will comprise 10 μgm/liter to 1000 μgm/liter.

The coolant tank 400 is now refilled with fresh coolant, and the combustion chamber recharged with cellulose. The process can now be repeated.

Normally the process can take place and the pyrolysis can be completed within one hour.

We have found that the efficiency of the apparatus and method described above enables one to produce smoke water which will work satisfactory using about one and a half kilograms of cellulose or biomass per liter of water.

It will be seen that the apparatus is capable of operating effectively and the smoke water is easy and clean to produce at sufficient levels to enable cost effective manufacture.

We have found that because of the extremely effective binding of the 3-methyl-2H-furo[2,3-c]pyran-2-one and the water for the reasons set forth above the smoke water thus formed comprises a more viable concentrate to provide a more effective end product.

It will be appreciated that the scrubber tends to be self cleaning which improves operation of the apparatus.

The invention is not limited to the precise constructional details hereinbefore described and illustrated. For example the 3-methyl-2H-furo[2,3-c]pyran-2-one may be formed in the combustion chamber 200 by the pyrolysis of any other biomass. If desired a low pressure pump may be provided to assist in drawing off the smoke from the combustion chamber 200 and leading it to the outlet pipe 208 and inlet head 210.

It will be understood that the various dimensions may vary as desired. For example in an industrial size apparatus, the combustion chamber may be of twenty cubic meters capacity to contain eight hundred kilograms of cellulose.

The inlet head 208 can be located at any position below the position in the primary scrubber 300 described above. Indeed the lower in the primary scrubber 300 that the smoke is discharged therein the greater the exposure of the smoke to the water droplets.

It will be appreciated that the cellulose can be wood that is suitably ground, leaf material and other organic fibre or any other combustible biomass may be used to form 3-methyl-2H-furo[2,3-c]pyran-2-one. The biomass may be in the form of amino acids. The compound 3-methyl-2H-furo[2,3-c]pyran-2-one may be formed as an amino carbonyl reaction between an amino containing compound and a sugar or may be synthetically produced. The starting liquid in the cooling tank may comprise other liquids such as aqueous alcohol.

If desired the smoke rising to the top of the scrubber may be lead to a secondary scrubber where it is subjected to a further mist scrubbing by smoke water discharged from the outlet 318 of the main scrubber whereafter it is passed to the cooler tank.

The invention claimed is:

1. An apparatus for making smoke water containing 3-methyl-2H-furo[2,3-c] pyran-2-one comprising:
    a combustion chamber capable of containing solid biomass and of burning the biomass therein to form smoke, the combustion chamber having a smoke conduit through which smoke from the burning biomass is discharged;
    a scrubber having
        a chamber with
            an inlet to which the smoke conduit is connected and
            an internal condenser having mist spray nozzles for spraying mist into the scrubber chamber to bind with the smoke entering the scrubber chamber to form condensed smoke solution; and
            an outlet for the condensed smoke solution, and
    a cooler connected to the outlet and thence to a maturation device for storage and or despatch of the smoke water.

2. The apparatus as claimed in claim 1 wherein the outlet is connected to the cooler through a filtering apparatus for removing impurities and solids.

3. The apparatus as claimed in claim 1 wherein the cooler is connected to a discharge unit through a line containing a filter device for removing impurities and solids.

4. The apparatus as claimed in claim 1 wherein the internal condenser is a spiral condenser.

5. The apparatus as claimed in claim 1 wherein the cooler is connected to the internal condenser to supply cooled aqueous smoke to the internal condenser to be discharged thereby through the spray nozzles.

\* \* \* \* \*